United States Patent [19]

Goldberg et al.

[11] Patent Number: 5,260,665
[45] Date of Patent: Nov. 9, 1993

[54] IN-LINE FLUID MONITOR SYSTEM AND METHOD

[75] Inventors: Jack Goldberg, San Diego; Kurt E. Zublin, Poway; Marl J. Bell, Valley Center, all of Calif.

[73] Assignee: IVAC Corporation, San Diego, Calif.

[21] Appl. No.: 693,357

[22] Filed: Apr. 30, 1991

[51] Int. Cl.$^5$ .............................................. G01F 1/68
[52] U.S. Cl. ................. 324/636; 73/861.95; 73/204.23; 604/65
[58] Field of Search ................ 324/636, 639; 73/19.1, 73/19.05, 61 R, 204.23; 604/50, 65; 128/653.1; 333/230, 246

[56] References Cited

U.S. PATENT DOCUMENTS

| | | | |
|---|---|---|---|
| 3,883,798 | 5/1975 | Free | 324/636 |
| 3,898,637 | 8/1975 | Wolstenholme | 340/239 |
| 4,014,206 | 3/1977 | Taylor | 73/19 |
| 4,211,987 | 7/1980 | Pan | 333/230 |
| 4,228,683 | 11/1980 | Juffa et al. | 73/204 |
| 4,237,730 | 12/1980 | Feng | 73/204 |
| 4,280,495 | 7/1981 | Lampert | 604/50 |
| 4,335,616 | 6/1982 | Oliva et al. | 73/861.05 |
| 4,423,623 | 1/1984 | Ho et al. | 324/639 |
| 4,483,200 | 11/1984 | Togawa et al. | 73/861.05 |
| 4,613,325 | 9/1986 | Abrams | 604/65 |
| 4,651,085 | 3/1987 | Sakurai et al. | 324/636 |
| 4,743,228 | 5/1988 | Butterfield | 604/65 |
| 4,866,370 | 9/1989 | Flemming et al. | 324/639 |
| 4,898,576 | 2/1990 | Philip | 604/50 |
| 4,912,982 | 4/1990 | Yukl | 324/636 |
| 4,938,079 | 7/1990 | Goldberg | 73/861.95 |

FOREIGN PATENT DOCUMENTS

| | | | |
|---|---|---|---|
| 8912228 | 12/1989 | European Pat. Off. | 73/19.1 |
| 0124445 | 5/1990 | Japan | 73/19.1 |

OTHER PUBLICATIONS

A Microwave Instrument for the Continuous Monitoring of the Water Content of Crude Oil, Proc. of IEEE, vol. 62, No. 1, Jan. 1974, Castle et al.

A Method for Measurement of the Permitivity of Thin Samples, Journal of Microwave Power, Jan. 1979, Stuchly, et al.

New Measurement Technique for the Dielectric Study of Solutions and Suspensions, Journal of Microwave Power, Jan. 1980, Berteaud.

*Primary Examiner*—Kenneth A. Wieder
*Assistant Examiner*—Maurak Regan
*Attorney, Agent, or Firm*—Fulwider, Patton, Lee & Utecht

[57] ABSTRACT

A non-invasive, in-line fluid monitor includes a segment of fluid line disposed such that it and the fluid within become a part of the dielectric loading on an energized electromagnetic sensor device. Perturbations of the dielectric loading on the sensor device are monitored to determine certain fluid properties, such as pressure, composition, and the presence of air. The fluid line segment disposed through the electromagnetic sensor may be compliant and thus changes size in response to fluid pressure, altering the volume of the fluid line segment tin the cavity and altering the dielectric loading on the cavity. In one embodiment, a resonant cavity is used to encompass the segment of fluid line and a processor is used to compare changes in the resonant characteristics of the cavity to predetermined data to determine the properties of the fluid. In an alternative embodiment, a transmission device such as a delay line is utilized as the sensor element, and in another embodiment, a microstrip resonator is utilized as the sensor element. In yet another embodiment incorporating a means of determining the volumetric fluid flow rate, the size of air bubbles in the fluid is assessed.

18 Claims, 7 Drawing Sheets

IN-LINE FLUID MONITOR SYSTEM AND METHOD

BACKGROUND

The invention relates generally to monitoring fluid in a line without direct fluid contact, and more particularly, relates to non-intrusively monitoring for changes in fluid properties, including the presence of air or other gas, and for fluid pressure.

In numerous medical and industrial applications, continuous in-line monitoring of a fluid is often necessary to ensure consistency of a process or to ensure safety. For example, the pressure of fluid in a line may be critical to a process. Additionally, the presence of air or other gas within a fluid or the presence of contaminants within a fluid may need to be monitored. Examples of non-medical applications for fluid monitoring can be found in the chemical process industry, where inexpensive and/or disposable fluid conduits may be required, where fluids may be present at high pressure, or where fluids which are highly caustic or highly toxic may be involved.

In the medical area, safety and cost are of great concern. Reliable and inexpensive in-line fluid monitoring without direct fluid contact is especially important in the medical area where sterilization and disposability of the fluid line are requirements. In fluid delivery systems with a positive pressure pumping mechanism, a flow path occlusion can be detected by monitoring the fluid pressure. When flow path disposability is required, fluid pressure is generally measured either by means of a disposable transducer or by means of a non-disposable transducer coupled with a disposable membrane or other compliant region arranged such that the transducer itself is not in direct contact with the fluid. Typically, a disposable transducer or specially designed transducer membrane is more expensive than a disposable fluid line alone. In regard to considerations of cost, it would be desirable to provide a pressure transducer which may be reused and disposable fluid lines which work with that transducer.

Air-in-line detection systems are used to prevent the inadvertent infusion of air into a patient's bloodstream. While small bubbles of air may have no adverse effect on a patient, large air bubbles can cause death. Methods for the in-line detection of air typically involve ultrasound or light transmission through the fluid line being monitored. The transmission characteristics of sound or light may be utilized as an indication of the presence of a gas bubble in liquid in the fluid line. Simple recognizable perturbations of the signals from such sensors may be utilized to trigger an alarm and/or halt the infusion. Such systems require that the fluid and the associated conduit be substantially transparent to the energy being transmitted. However, due to their inability to reliably distinguish between air bubbles of varying sizes, ultrasonic or optical air-in-line detectors sometimes behave erratically, falsely indicating the presence or absence of air bubbles. Typically, such sensors cannot determine the exact size of air bubbles and are configured merely to indicate the presence of air bubbles which are greater than a predetermined size.

Other apparatus capable of detecting impurities such as air within a fluid include electrochemical systems and laser doppler systems. Electrochemical systems can be extremely sensitive to specific compositional variations in a fluid, but incorporate components, such as membranes, which must be in direct contact with the fluid, thus increasing their costs in applications requiring disposability. Laser systems are at present very expensive, and still other systems cannot operate over the wide range of flow rates and fluid types required in many applications.

Hence those concerned with fluid line monitoring have recognized that it would be beneficial to provide an in-line fluid monitoring system and method which does not involve direct fluid contact with a sensor but which exhibits higher sensitivity to variations in fluid composition, including the presence of air or other gas, and which can provide an indication of the size of a gas bubble. In medical systems, there is a need for an apparatus and method which reliably and accurately detect and quantify the presence of air or other impurities in the line but at the same time are relatively inexpensive and can function with an inexpensive disposable fluid line. Additionally, in medical systems, there is a need for an apparatus and a method which can reliably and accurately measure the pressure within an inexpensive disposable fluid line. The present invention fulfills these needs.

SUMMARY OF THE INVENTION

The present invention provides for in-line fluid monitoring without direct fluid contact. Detection of fluid properties, including the presence of air or other gas and the indication of changes in fluid composition, as well as the determination of fluid pressure are provided. The fluid monitor in accordance with the invention includes the use of a segment of fluid line disposed such that it becomes a part of the dielectric loading of an electromagnetic sensing device. The dielectric loading is monitored to determine the fluid properties such as the composition and pressure of the fluid in the fluid line segment. In one embodiment, a resonant electromagnetic sensing device is incorporated into an oscillation circuit and the frequency of oscillation is monitored. Changes in that frequency are used to determine fluid pressure and composition, including the presence of air or other gas in the fluid.

In one embodiment, a resonant electromagnetic cavity, such as a microwave cavity, is used to encompass a compliant segment of the fluid line. Because the fluid line is compliant, the volume of fluid within the cavity varies in accordance with fluid pressure. The compliant segment and fluid therein are used to form a part of the dielectric loading of the cavity and this dielectric loading is monitored to determine the pressure and composition of the fluid. In circumstances where pressure measurement is not required, the fluid line segment is preferably non-compliant. Circuitry is provided which forms an oscillator whose resonant element is the cavity itself and thus changes in the dielectric loading of the cavity produce variations in the oscillating frequency. Perturbations of the oscillating frequency are monitored and indicate changes in fluid pressure and composition. In one embodiment, the electric field in the cavity is focused on the segment of fluid line encompassed by the cavity so that the fluid line accounts for the major portion of dielectric loading of the cavity.

A processor is used to compare changes in the oscillating frequency to predetermined parameters to determine the changes in the composition and pressure of the fluid in the segment of the fluid line. A look-up table may be provided in the processor so that certain changes in the oscillating frequency may be correlated with fluid composition and pressure and such changes indicated to the user. For example, an inhomogeneity such as a small air bubble presents a markedly different dielectric load than surrounding liquid and thus its presence in the sensor cavity is accompanied by a large shift in the oscillating frequency.

In one embodiment, volumetric flow data of the fluid in the fluid line is furnished. By knowing the volumetric flow rate, the size of the air bubbles in the fluid line can be assessed.

Other aspects and advantages of the invention will become apparent from the following detailed description and the accompanying drawings, illustrating by way of example the features of the invention.

DETAILED DESCRIPTION OF THE PREFERRED EMBODIMENTS

Figure 1:
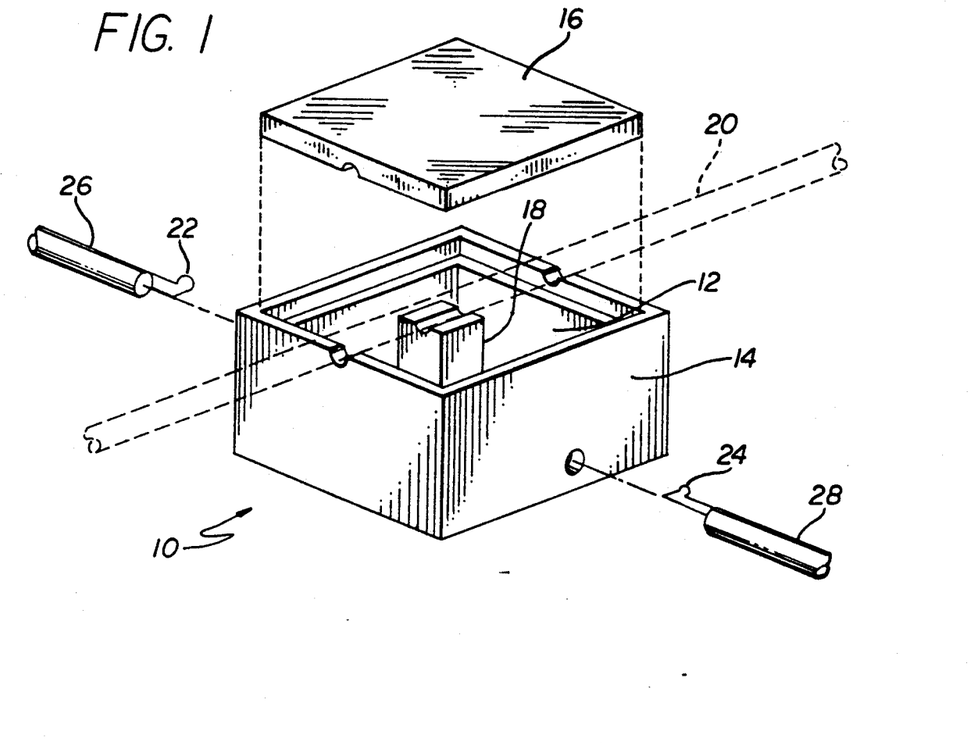
FIG. 1 shows an exploded, perspective three-dimensional view of a two-port resonant cavity having a fluid line traversing it in accordance with the principles of the invention and having an electric field in a focused region parallel to the fluid line.
Figure 2:
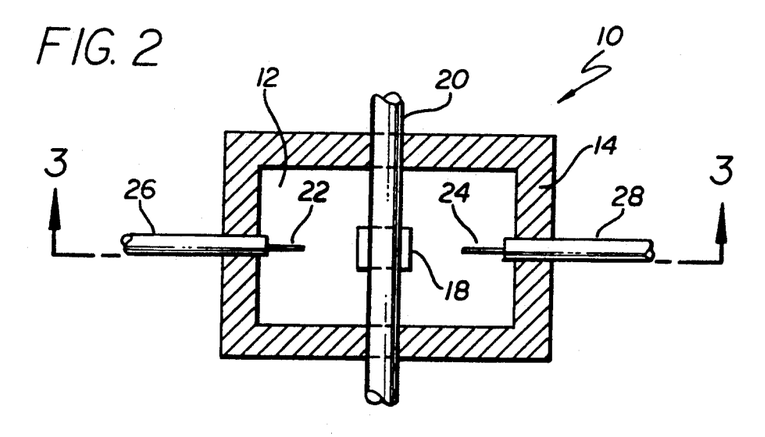
FIG. 2 is an assembled, top sectional view of the resonant cavity of FIG. 1 with the cover removed.
Figure 3:
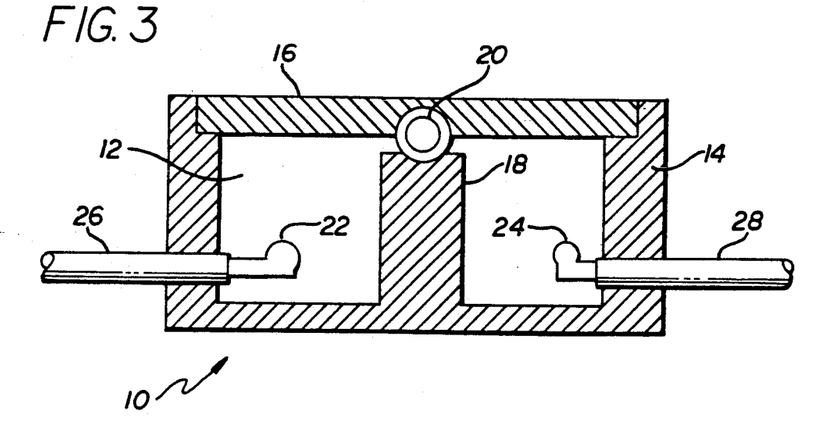
FIG. 3 is an assembled, side sectional view of the resonant cavity of FIG. 1 taken along lines 3—3 of FIG. 2.

Referring now to the drawings with more particularly, wherein like reference numerals designate like or corresponding elements among the several views, there is shown in FIGS. 1 through 3 a resonant cavity device 10 having a cavity 12 formed by five walls 14 which in this embodiment are formed of an electrically conductive metal such as copper or brass. A cover 16 is fitted onto four of the walls 14 to form a sixth wall thereby making cavity 12 a closed cavity.

The cavity device 10 includes a focusing post 18 placed within the cavity 12 for focusing energy imparted to the cavity into a segment of fluid line 20 which is mounted such that it proceeds through the cavity device 10 and is proximate to the focusing post 18. As shown more clearly in FIG. 1, the cover 16, two of the sides 14 and the focusing post 18 have been formed with indentations so that the fluid line 20 can be supported while it proceeds through the cavity device 10. These indentations effectively form a channel through the cavity device 10 in which the fluid line segment is disposed. In the case where fluid pressure is measured, the fluid line is compliant and its expansion or contraction must not be hindered due to physical contact with either the focusing post 18 or the cavity cover 16. Also shown in FIGS. 1 though 3 is the use of two probes 22 and 24 which are used to feed energy to and from the cavity 12. In this embodiment, the probes are coupling loops supported in the cavity 12 by respective cables 26 and 28 or supported by other means.

An alternative resonant cavity embodiment incorporates a cavity constructed of plastic with metallized inner surfaces. Another alternative resonant cavity embodiment incorporates a plastic-filled cavity with metallized outer surfaces and a metallic focusing post electrically connected to the metallized outer surface. In these cases, provision must be made to accommodate the fluid-filled line to be disposed therein as well as the two probes.

The cavity device 10 forms a resonant cavity 12 energized by a transmitter probe 22. The receiver probe 24 couples energy from the cavity for processing as will be described in more detail below. Such a cavity will resonate at a frequency dependent upon the cavity size, configuration and the dielectric properties of the "medium" in the cavity 12. In addition, other resonant characteristics such as bandwidth and Q as well as the impedance of the cavity can be affected by dielectric loading. The captured segment of fluid line and fluid therein form a part of the cavity medium and changes occurring in that fluid line and fluid will affect the dielectric properties of the medium. Thus, changes in the fluid composition and changes in the volume of segment 20 of the fluid line will alter the dielectric loading and cause a consequent change in the resonant characteristics of the cavity 12. By monitoring the cavity's resonant characteristics, certain fluid properties can be determined.

In one embodiment, the transmission probe 22 imparts a small amount of electromagnetic energy (less than one milliwatt) to the cavity at a microwave frequency; for example 5.0 GHz. Because of the transmission probe's geometry, size, location and orientation, when energy is introduced into the cavity at or near its fundamental resonant frequency, the focusing post 18 will cause a localized electric field to be produced in the region between the top of the post 18 and the cover 16. The electric field is focused on the segment of fluid line 20 and the fluid therein. In this embodiment, the cavity structure is such that the fluid line is disposed perpendicular to the electric field. One purpose of the focusing post is to cause the fluid line segment 20 to be the major determinant of the dielectric loading of the cavity 12. Small changes in the fluid line 20 and fluid therein will significantly affect the dielectric loading of the cavity. Thus, the sensitivity of the monitor is increased.

The cavity 12 acts as a filter in that energy at or near particular frequencies, such as the fundamental resonant frequency of the cavity, will be efficiently imparted to the fluid. The resonant characteristics of the cavity, which is surrounding the fluid line segment filled with a fluid, will remain stable as long as the parameters which are responsible for determining the cavity's resonant characteristics remain constant. However, should the dielectric properties of the fluid within the focused region of the electric field within the cavity change, or the volume of the fluid within the focused region of the electric field change, an accompanying change in resonant characteristics will also occur.

Figure 4:
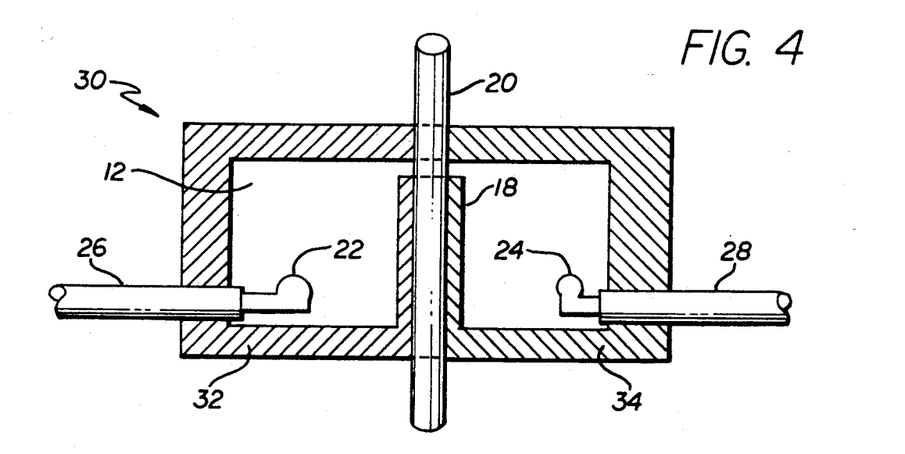
FIG. 4 is a cross-sectional view of a resonant cavity having a fluid line traversing it such that an electric field in a focused region is parallel to the fluid line.

Although shown as a rectangularly shaped cavity with coupling loops for feeds, other cavity shapes and feed devices may be used. Those shown in FIGS. 1 through 3 are for purposes of illustration only and depict a cavity structure wherein the fluid line 20 is disposed perpendicular to the electric field in the focused region. In FIG. 4, a cross-sectional view of an alternative resonant cavity structure 30 is shown in which the fluid line 20 is disposed parallel to the electric field in the focused region. Such a sensor is constructed in a manner which allows the fluid line to be properly installed; for example, the cavity may be split symmetrically along the axis of the fluid line 20 into two halves 32 and 34 and a clamping mechanism (not shown) provided for electrical contact and mechanical stability.

Additionally, although a cavity is shown as the dielectrically-loaded electromagnetic filter device used, other filter devices may be used. For example, in applications where large changes in fluid composition or large pressure excursions, such as +800 to −250 mm mercury, need to be monitored, a sensor based on the monitoring of dielectric loading, but of lower sensitivity than the cavity type, can be utilized.

Figure 5:
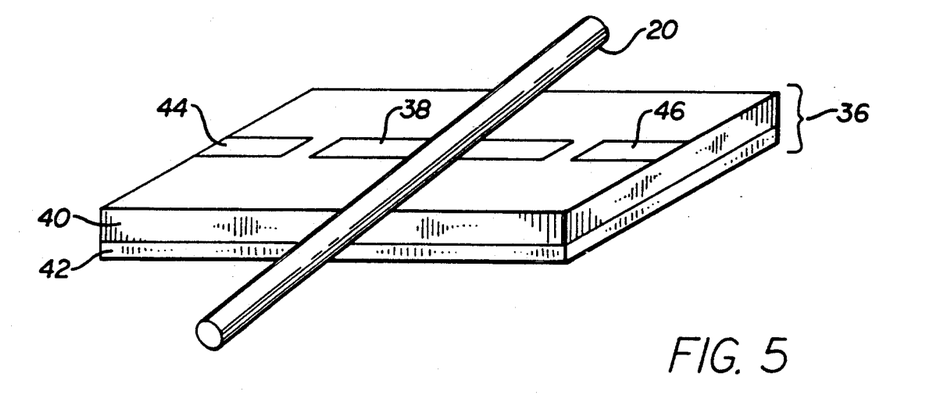
FIG. 5 is a diagram of a microstrip resonator with a fluid line segment disposed such that it forms a part of its dielectric load.

In another embodiment, instead of using a cavity resonator with the electromagnetic field enclosed, an open planar microstrip or stripline resonant structure can be employed. In FIG. 5, there is shown a microstrip resonator device 36 with the resonant microstrip line element 38 supported by the substrate 40, which is backed by the ground plane 42. Two microstrip line elements 44 and 46 form the input and output coupling ports. The fluid line segment 20 is disposed over the resonant element 38 at or near the region of maximum electric field and thus forms a part of the dielectric loading of the resonator. When resonating in its fundamental resonant mode, for example, the electric field that is generated has its maximum amplitude at the center of the resonating element 38. Any changes in dielectric loading caused by a change in fluid composition, the presence of air or other gas, or changes in fluid volume will therefore perturb the resonant characteristics in an identifiable manner.

Figure 6:
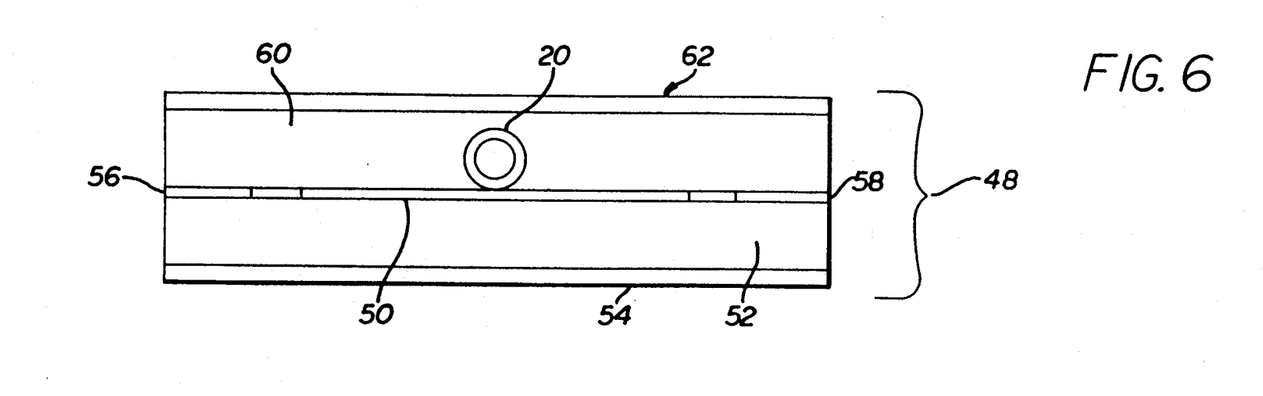
FIG. 6 is a cross-sectional view of a modified stripline resonator with a fluid line segment disposed such that it forms a part of its dielectric load.

Although FIG. 5 illustrates an open microstrip resonator, a shielded configuration may be used in another embodiment. In FIG. 6, a modified stripline resonator 48 is illustrated. In this case, a resonant stripline element 50 is supported by the lower substrate 52, which is backed by a ground plane 54. Two stripline elements 56 and 58 form the input and output coupling ports. The fluid line segment 20 is disposed over the resonant element 50 at or near the region of maximum electric field and is sandwiched between the lower substrate 52 and the upper substrate 60. The upper substrate 60 is backed by a second ground plane 62. The two ground planes 54 and 62 together provide greater shielding than in a microstrip structure. An appropriate channel must be cut into the upper substrate 60 to accommodate the fluid line segment. As the fluid line 20 is disposed such that it forms a major part of the dielectric loading of the resonator, changes in the composition and/or pressure of the fluid within will perturb the structure's resonant characteristics.

Figure 7:
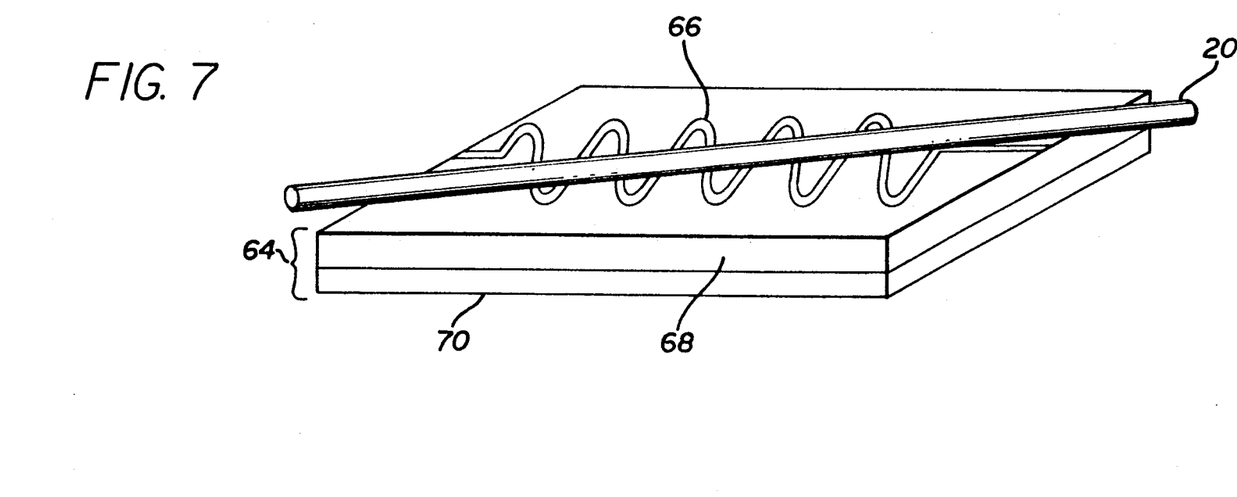
FIG. 7 is a diagram of a fluid line segment disposed so that it forms a part of the dielectric loading of a microstrip delay line.

In yet another embodiment, a dielectrically-loaded electromagnetic transmission device may be employed as the sensing element rather than a filter device. In FIG. 7 there is shown a microstrip delay device 64 over which is disposed the fluid line segment 20. The transmission element 66 is supported by the substrate 68 which is backed by ground plane 70. The fluid line segment 20 is disposed in a manner which allows the electromagnetic field created by the energized transmission element 66 to encompass a significant portion of the fluid line segment. Thus the fluid line segment and fluid within form a part of the dielectric loading of the delay device. An alternative to the microstrip transmission device would be a modified stripline transmission device. Although, in these cases, the transmission devices do not act as filters, as in the cavity embodiment, they do use the dielectric loading imparted by the fluid line segment and fluid therein and may be used to determine changes in the fluid composition and/or pressure.

Each fluid possesses particular dielectric properties. When different fluids are mixed together, a new fluid is formed that will probably possess different dielectric properties from the two separate fluids. Moreover, gases, such as air, possess radically different dielectric properties than that of liquids. Water, for example has a dielectric constant approximately eighty times higher than that of air. Thus, referring to the resonant cavity embodiment of FIGS. 1 through 3, the presence of air bubbles in a liquid will cause a radical change in the dielectric loading of the cavity. This change in dielectric properties will cause a significant and identifiable change in the filtering characteristics of the cavity.

Referring again to FIGS. 1 through 3, when compliant tubing is used as the section of fluid line 20, an increase or decrease in fluid pressure will cause the tubing to expand or contract accordingly and the fluid volume within the cavity at the focused region of the resonant cavity will change. This change in volume causes a change in the dielectric loading of the resonant cavity and will cause a change in the cavity's filtering characteristics. By this arrangement, the in-line fluid monitor can determine fluid pressure.

Figure 8:
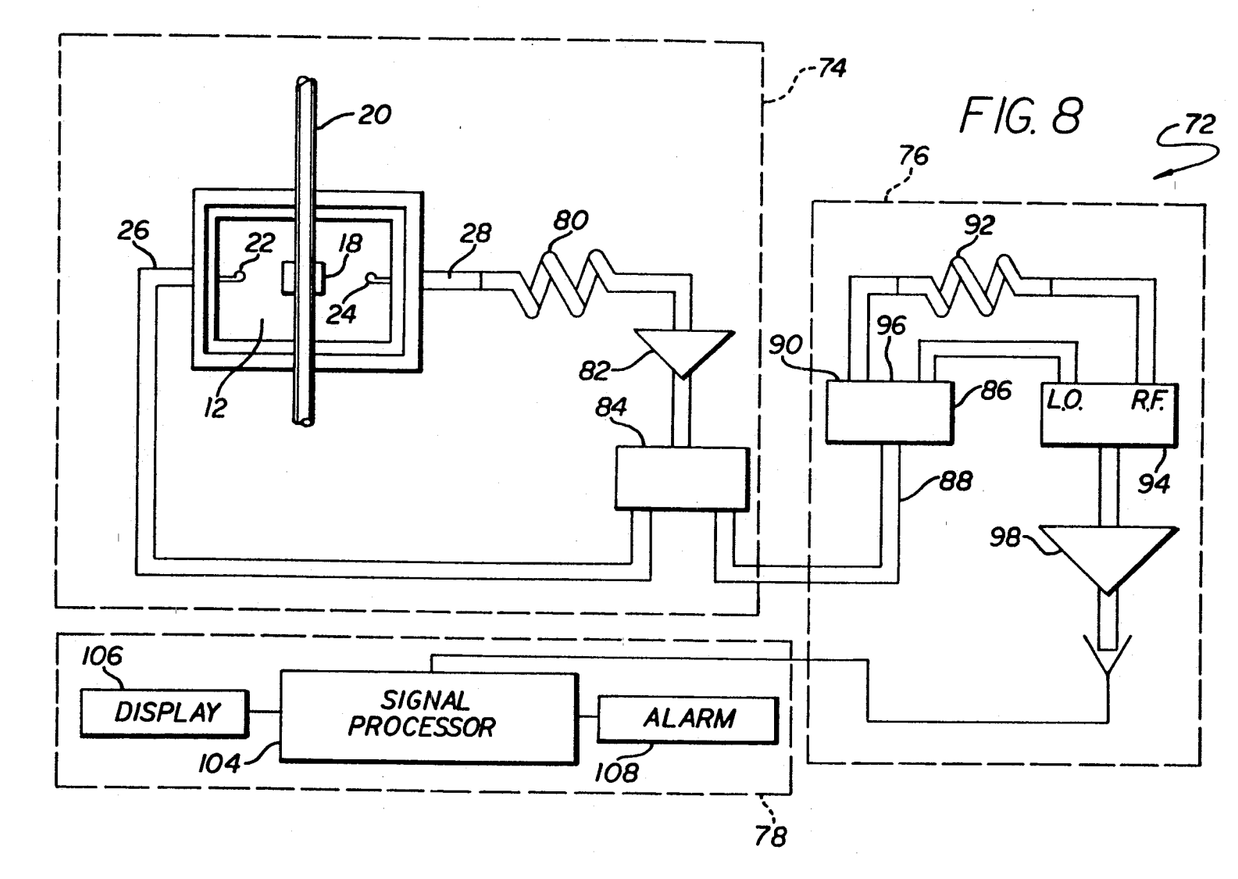
FIG. 8 is a block/schematic diagram of an in-line fluid monitor system in accordance with the principles of the invention.

A schematic/block diagram of an in-line fluid monitor system 72 in accordance with the principles of the invention is shown in FIG. 8. The circuit 72 generally comprises three main functional blocks, the sensor oscillator block 74, the discriminator block 76, and the processing block 78. The sensor block 74 contains the resonant cavity 12.

The sensor oscillator block 74 is used to provide a signal representative of the fluid characteristics (e.g., presence of air or other gas in the line, changes in fluid composition, pressure), and comprises a sensor delay element 80 connected to the sensor output cable 28, a bandwidth-limited amplifier 82 connected to the delay element 80, a coupler 84 which receives the output of the amplifier 82 and directs a portion of the output from the amplifier 82 to the input cable 26 of the resonant cavity 12. The coupler 84 also directs a portion of the output from the amplifier 82 to the discriminator circuit 76. Thus, a circuit is formed in sensor oscillator block 74 wherein the energy of the amplifier is coupled to the resonant cavity 12 via the coupler 84 and the input cable 26 and coupling loop 22. Energy is then coupled through the cavity 12 which surrounds a portion of the fluid path 20 and the fluid. The output coupling loop 24 then couples energy from the cavity 12 to the delay element 80 and to the input of the amplifier 82. The power level in the sensor oscillator block 74 is low (less than one milliwatt in one embodiment) so that the fluid characteristics can be "interrogated" and the fluid not appreciably heated. In the preferred embodiment, the bandwidth of amplifier 82 is limited such that oscillations in the primary (fundamental) resonant mode of the cavity are sustained and oscillations at higher modes are suppressed.

In order to sustain oscillation, the output of the amplifier 82 must supply positive feedback to its input. An additional requirement for oscillation is that the gain of the sensor oscillator block 74, the "loop gain", must be greater than one, that is, the gain in the amplifier must be greater than the sum of the losses of the components in the loop. This gain is sufficient to initiate stable oscillation quite rapidly, on the order of microseconds or less. The frequency of the oscillator block is determined primarily by the resonant characteristics of the cavity and the total delay around the loop from amplifier output to amplifier input, as well as the gain of the loop. Thus, changes in the dielectric loading of the cavity due to changes in fluid composition, including the presence of air of other gas, and/or pressure (volume) within the focused region of the cavity will result in a change in oscillation frequency.

The discriminator block 76 processes the oscillation signal and includes a signal splitter 86 which receives a portion of the output from the sensor amplifier 82 through the coupler 84 and a discriminator input line 88. The discriminator signal splitter 86 has an output 90 to a delay element 92 which is connected to one port of a phase detector 94, such as the R.F. port of a double-balanced mixer, and the discriminator signal splitter also has an output 96 which is connected to the L.O. port of the double balanced mixer. The output from the double balanced mixer 94 (phase detector) is directed to a low frequency amplifier 98 capable of amplifying signals from D.C. to a frequency consistent with the rate of fluid property changes which are being monitored. The amplifier 98 has an output which is provided to the signal processor block 78. The discriminator delay element 92 may alternatively be an appropriate phase shifting reactive element, and although the mixer/amplifier arrangement is provided to convert changes in frequency of the sensor oscillator block 74 to changes in voltage, other types of conversion to a signal suitable for analysis by the signal processor block 78 may also be used.

Figure 9:
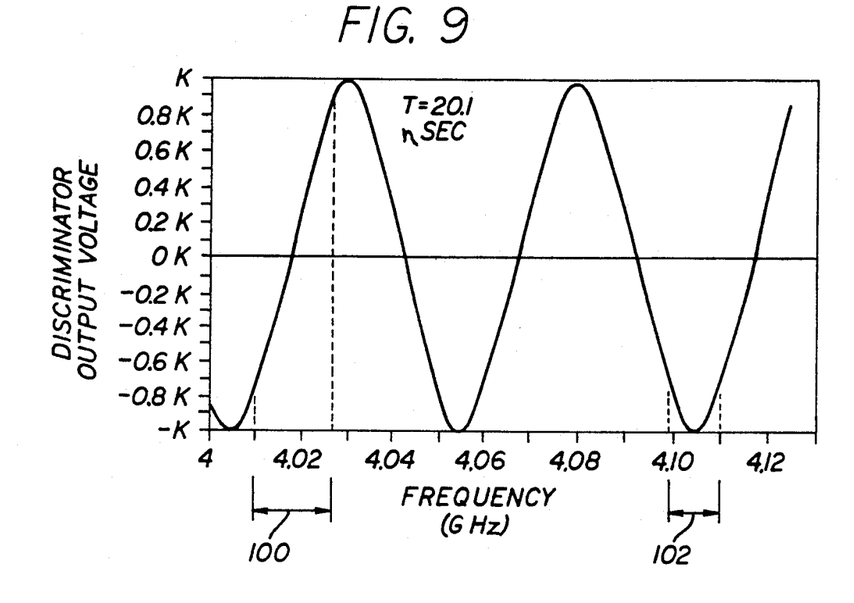
FIG. 9 is a chart of the output voltage of a discriminator versus frequency.

Operation of the frequency discriminator block 76 can be described by simple mathematical relationships. Given that F is the oscillating frequency of the cavity 12 in Hertz, and that the delay element 92 provides a delay T in seconds, the output of the discriminator is ideally equal to $K\cos(2\pi FT)$, where K is a gain constant depending on the amplitude of oscillation and other circuit details. For example, for F=4.02 GHz and T=20.1 nanoseconds, the discriminator output would be 0.321K. If the oscillating frequency is perturbed to 4.025 GHz, the resulting output of the discriminator would be 0.818K. The delay element 92 is chosen such that the discriminator sensitivity is high in the frequency region of operation. It was found that near frequencies where $\cos(2\pi FT)=0$, the best sensitivity exists; poor sensitivity exists near frequencies where $\cos(2\pi FT)=+1$ or $-1$. In the specific case outlined above, good sensitivity exists in the range of from 4.0 GHz to 4.025 GHz. FIG. 9 illustrates the relationship between discriminator 76 output voltage and oscillating frequency, for the particular case of T=20.1 nanoseconds in the frequency range of from 4.0 GHz to 4.12 GHz. The range 100 represents a high sensitivity discrimination frequency sensing range, and the range 102 represents a low sensitivity discrimination frequency sensing range.

When normal fluid characteristics exist within the resonant cavity, the delay line 92 in the discriminator block 76 is adjusted so that an output of zero volts is produced at the output of the mixer 94. Referring again to FIG. 9, it can be seen that this is the steepest part of the discriminator 76 output, thereby yielding the highest sensitivity.

Once the change in frequency has been converted to a change in voltage, it is amplified 98. The electrical signals supplied by the discriminator block 76 of the in-line fluid monitor 72 must be processed or analyzed in order to determine and quantify important fluid characteristics. Preferably, this task is implemented by a microprocessor included as part of the signal processor 104. As a great many instruments currently produced incorporate a microprocessor, the signal processing requirement of this in-line fluid monitor do not represent a large cost. In industry and in hospital fluid delivery, microprocessors perform many computational and control tasks, including communications with the operator of the instrument, allowing the operator to intelligently interact with the instrument in setting desired parameters and limits. Additionally, the microprocessor can easily perform the calculations necessary for "closed loop control", where a desired pressure can be maintained by controlling a pumping mechanism.

In the preferred embodiment, the signal processor 104 receives the electrical output signal from the discriminator block 76, which represents the oscillating frequency of the resonant cavity 12. The microprocessor can make determinations based on changes to the oscillating frequency. The existence of a small amount of air in the fluid line segment can be determined by comparing the frequency change to parameters that are either fixed, or "entered in" by the operator of a system which utilizes the in-line fluid monitor. The signal processor 104 includes conventional circuitry and programming for comparing the discriminator output voltage signal with a reference value and for determining the magnitude of perturbation of the oscillating frequency. The signal processor 104 is also preferably constituted so as to provide an output signal either to a display and/or printer unit 106, such as a display monitor for viewing a real time graph of waveforms of the perturbation of oscillations in the resonant cavity 12, and the signal processor may be adapted to simultaneously generate a signal to an alarm device 108, for indicating an alarm condition when the magnitude of perturbation is greater than a predetermined threshold value. The alarm device 108 may aurally indicate an alarm and may also be coupled to the pump controller to automatically stop pump operation.

Figure 10:
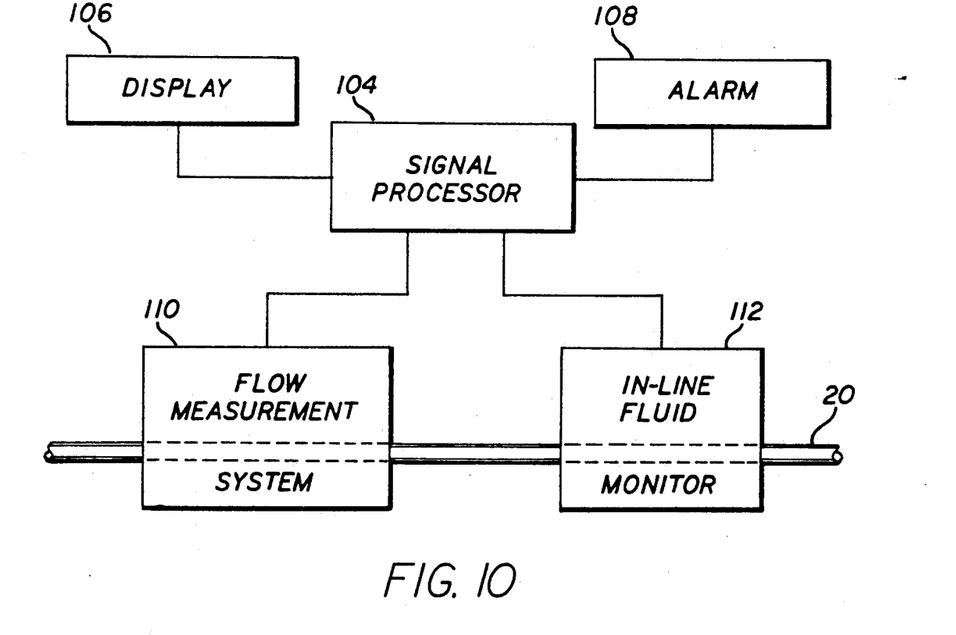
FIG. 10 is a block diagram of an in-line fluid system which includes volumetric flow data of the fluid in a fluid line and an in-line fluid monitor coupled to the same fluid line and a common processor to determine the size of gas bubbles.

Referring now to FIG. 10, a volumetric flow rate data source 110 provides data representative of the volumetric flow rate of the fluid in the fluid line 20 to the signal processor 104. The in-line fluid monitor 112 is also coupled to the signal processor 104 for providing fluid property data as described above. By knowing the volumetric flow rate of the fluid, the size of detected bubbles can be assessed. This feature can provide important information in a medical infusion and permits the operator to monitor the infusion process more accurately. This is important in sensitive applications such as infusing fluid to a neonate where even small air bubbles can be fatal. In one embodiment, the volumetric flow rate data is provided by the electronic control system which operates a precision fluid pumping mechanism. In another embodiment, a flow meter may be provided to provide the flow data, such as that disclosed in U.S. Pat. No. 4,938,079 to Goldberg.

Figure 11:
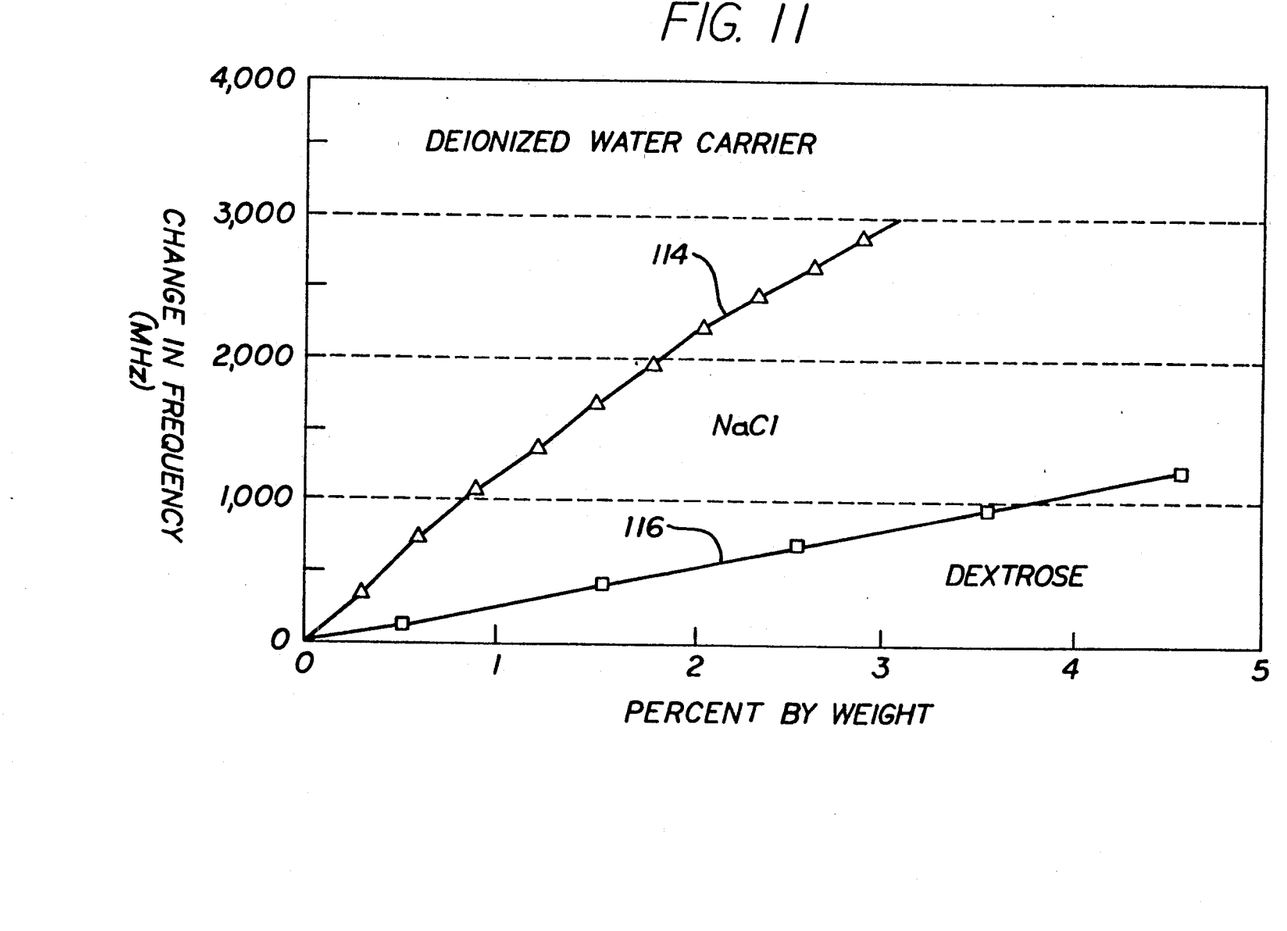
FIG. 11 is a sample graph illustrating the change in oscillating frequency due to changes in concentration of fluid constituents.

Because changes in the dielectric loading can be detected, changes in fluid composition can be detected. Varying concentrations can also be detected as is illustrated in FIG. 11, where varying concentrations of both sodium chloride 114 and dextrose 116 in water produce a change in frequency. Although not shown, radical changes in frequency accompany the presence of a gas in the liquid.

Another feature of the system is the ability to detect impurities, or contaminants other than air, such as blood. As an impurity passes through the sensor, the filtering characteristics of the cavity change. Blood has a notably different dielectric character than most common infusates, such as sodium chloride solution, so that if blood were to back up into the administration set, its presence could be detected by observing the perturbation of the oscillation frequency. In addition, if two or more different fluids were to be infused successively through the same line, the sensor could detect the perturbation of the cavity loading, assuming the fluids have different dielectric characters, in order to verify that the changeover between fluid types was successful.

In actual practice, the change in dielectric loading caused by the presence of air in the line is so great, that a system of the type shown in FIG. 8 may cease to oscillate while a large amount of air is within the sensing region of the cavity. The range of possible oscillation frequencies at which the system can oscillate depends largely on the bandwidth of the amplifier 82. This bandwidth must be chosen such that oscillation is supported whenever a bubble of a size which the user needs quantified passes through the cavity. For bubbles that are so large that oscillations cease, the signal processor 104 will preferably initiate an alarm 108. Depending on the size of the bubble, frequency shifts from 0.1 MHz to 400 MHz have been observed in practice.

When a polyurethane tubing of 0.105" inner diameter and 0.145" outer diameter is utilized, pressure change of the order of ±300 mm mercury, for example, causes oscillating frequency changes in the range of ±3 MHz. This frequency shift is generally less than that caused by the passage of an air bubble of significant size. Pressure change can also be distinguished from air bubble passage because the frequency changes due to pressure change are far less abrupt than those caused by air bubble passage. Although frequency shifts due to fluid compositional changes overlap the range of frequency shifts caused by pressure change, those caused by compositional variations are generally not transient in nature. When a fluid type changeover takes place, for example, the signal processor 104 is programmed to expect a frequency change which is sustained for the duration of the infusion or until a subsequent changeover takes place, rather than a transient change as may take place when the pressure varies.

Figure 12:
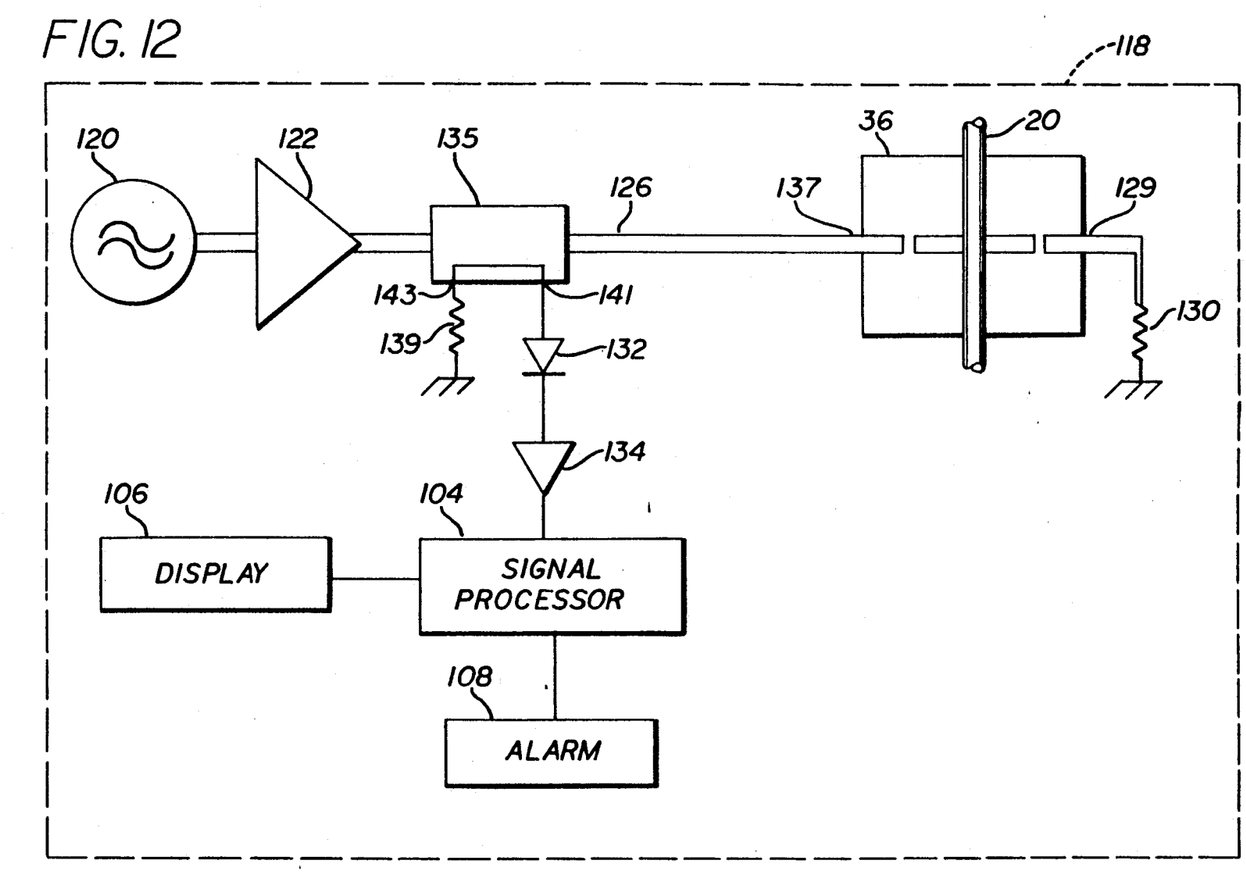
FIG. 12 presents another embodiment of an in-line fluid monitor system utilizing a dielectric resonator oscillator as the signal source.

Another embodiment of an in-line fluid monitor system 118 in accordance with the principles of the invention is illustrated in a schematic/block diagram of FIG. 12. A stable frequency source 120, such as a dielectric resonator oscillator (D.R.O.) is used, and is shown driving an amplifier 122 the output of which produces sufficient power for sensor operation, for example 10 dBm. The power from the amplifier is then fed through a quarter-wavelength directional coupler, such as a microstrip coupler 135, to the input port 137 of a microstrip resonator 36, which may be similar to that described above in relation to FIG. 5. The fluid line 20 and fluid therein are positioned to dielectrically load the resonator 36. The output port 129 of the resonator 36 is coupled to a signal return through a load 130, which is shown as a fifty ohm resistor in this case.

The directional coupler 135 is arranged such that it is responsive to the reflected power from the input port 137 of the microstrip resonator 36. Proper termination, shown to be a fifty ohm resistor 139 in this case, is provided at the terminated port 143 of the directional coupler 135, and the reflected power from the resonator 36 is monitored with a detector, such as a diode detector 132 at the reflected power port 141 of the coupler 135. The diode detector 132 may be thought of as a first processor and the signal developed by the detector 132 is amplified 134 and coupled to the signal processor 104. In the embodiment of FIG. 12, the amplitude of the reflected power at port 141 is affected by the dielectric loading on the resonator 36. Changes in that dielectric loading caused by fluid property changes will be detected by detector 132 and provided to the processor 104. The arrangement of FIG. 12 may incorporate a rigid fluid line segment 20 over the resonator 36 and can be used to determine the existence of an air bubble in the fluid line.

From the foregoing, it will be appreciated that the in-line fluid monitor system and method in accordance with the principles of the invention provides a simple, cost effective, and accurate way of detecting fluid properties and pressure. The fluid line may be disposable while the monitor system can be reused.

Although specific embodiments of the invention have been described and illustrated it is clear that the invention is susceptible to numerous modifications and embodiments within the ability of those skilled in the art, and without the exercise of inventive faculty. Thus, it should be understood that various changes in form, detail and application of the present invention may be made without departing from the spirit and scope of the invention.

We claim:

1. An apparatus for monitoring fluid in a fluid line, the apparatus comprising:
   a compliant fluid line segment coupled to the fluid line such that the fluid flows through the segment;
   a dielectrically loaded electromagnetic sensing device coupled to the compliant segment such that the segment and fluid therein provide dielectric loading on the sensing device, the sensing device providing a sensor signal representative of the dielectric loading;
   a flow data source which provides a flow signal representative of the volumetric flow rate of the fluid in the fluid line; and
   a processor, having predetermined gas data representative of a gas in the fluid, which receives the sensor signal from the sensing device, provides a loading signal representative of the dielectric loading, compares the loading signal to the predetermined gas data to detect the presence of the gas and upon detecting the gas, determines the time period that the sensing device detects the gas and processes the detection time period with the flow signal and provides a signal indicative of the size of the gas bubble.

2. The apparatus of claim 1 wherein:
the predetermined data comprises data representing a solute in the fluid; and
the second processor compares the loading signal to the predetermined solute data and provides a signal representative of the concentration of the solute in the fluid.

3. An apparatus for monitoring fluid in a fluid line, the apparatus comprising:
a dielectrically loaded resonant electromagnetic sensing device coupled to a segment of the fluid line such that the segment and fluid therein form part of the dielectric loading on the sensing device, the sensing device provides a sensor signal representative of the dielectric loading;
a flow data source which provides a flow signal representative of the volumetric flow rate of the fluid in the fluid line;
a processor, having predetermined gas data representative of a gas in the fluid, which receives the sensor signal from the sensing device, provides a loading signal representative of the dielectric loading, compares the loading signal to the predetermined gas data to detect the presence of the gas and upon detecting the gas, determines the time period that the sensing device detected the gas, processes the detection time period with the flow signal and provides a signal indicative of the size of the gas bubble.

4. The apparatus of claim 3 wherein the dielectrically loaded resonant device comprises a resonant cavity having an electric field and a focusing post which focuses the electric field onto the segment of fluid line such that the segment provides a substantial part of the dielectric loading of the cavity.

5. The apparatus of claim 3 wherein:
the resonant device comprises a microstrip resonator;
the fluid line segment is disposed to provide dielectric loading to the microstrip resonator; and
the sensor signal represents the dielectric loading of the microstrip resonator.

6. The apparatus of claim 3 wherein:
the resonant device comprises a stripline resonator;
the fluid line segment is disposed to provide dielectric loading to the stripline resonator; and
the sensor signal represents the dielectric loading of the stripline resonator.

7. An apparatus for monitoring fluid in a fluid line, the apparatus comprising:
a dielectrically loaded electromagnetic sensing device having a planar structure and coupled to a segment of the fluid line such that the segment and fluid therein provide dielectric loading on the sensing device, the sensing device provides a sensor signal representative of the dielectric loading;
a processor having predetermined gas data representative of a gas in the fluid, which receives the sensor signal from the sensing device, provides a loading signal representative of the dielectric loading, compares the loading signal to the predetermined gas data to detect the presence of the gas and provides a signal indicative of the gas detection.

8. The apparatus of claim 7 wherein the planar sensing device comprises a resonant device, a resonant characteristic of which varies in response to the dielectric loading;
the segment is disposed to provide dielectric loading to the resonant device;
the sensor signal is responsive to the resonant characteristic; and
the processor provides the loading signal in response to the resonant characteristic.

9. The apparatus of claim 8 wherein:
the planar sensing device comprises a microstrip resonator;
the segment is disposed to provide dielectric loading to the microstrip resonator; and
the sensor signal represents the dielectric loading of the microstrip resonator.

10. The apparatus of claim 8 wherein:
the planar sensing device comprises a stripline resonator;
the segment is disposed to provide dielectric loading to the stripline resonator; and
the sensor signal represents the dielectric loading of the stripline resonator.

11. The apparatus of claim 7 wherein:
the planar sensing device comprises a transmission device, the delay through which varies in response to the dielectric loading;
the segment is disposed to provide dielectric loading to the transmission device;
the sensor signal is responsive to the delay through the transmission device; and
the processor provides the loading signal in response to the delay.

12. A method of monitoring fluid in a fluid line, comprising the steps of:
forming a segment of the fluid line of complaint material;
sensing the volumetric flow rate of the fluid in the fluid line and providing a flow signal representative of the rate;
disposing the compliant segment such that it and the fluid therein provide dielectric loading on a sensing device;
sensing the dielectric loading of the sensing device;
providing a loading signal which is representative of the sensed dielectric loading of the sensing device;
comparing the loading signal to predetermined gas data which is representative of a gas in the fluid to detect the presence of the gas and upon detecting the gas, processing the time period that the gas is detected with the flow signal and providing a signal indicative of the size of the gas bubble passing through the fluid line in response to said comparison.

13. A method of monitoring fluid in a fluid line, comprising the steps of:
disposing a segment of the fluid line such that it and the fluid therein provide dielectric loading on a resonant electromagnetic sensing device, a resonant characteristic of which varies in response to the dielectric loading;
sensing the resonant characteristic of the sensing device;
providing a loading signal which is representative of the sensed resonant characteristic of the sensing device;

sensing the volumetric flow rate of the fluid in the fluid line and providing a flow signal representative of the rate; and comparing the loading signal to predetermined gas data which is representative of a gas in the fluid, to detect the presence of the gas and upon detecting the gas, processing the time period that the gas is detected with the flow signal and providing a signal indicative of the size of the gas bubble passing through the fluid line in response to the comparison.

14. The method of claim 13 further comprising the steps of:

providing a resonant cavity as the resonant device;
forming an electric field in the cavity; and
focusing the electric field onto the compliant segment of fluid line such that the segment forms a substantial part of the dielectric loading of the sensing device.

15. The method of claim 13 further comprising the steps of:

providing a microstrip resonator as the resonant device;
disposing the fluid line segment to provide dielectric loading to the microstrip resonator;
monitoring a resonant characteristic of the microstrip resonator; and
providing the loading signal in response to the resonant characteristic.

16. The method of claim 13 further comprising the steps of:

providing a stripline resonator as the resonant device;
disposing the fluid line segment to provide dielectric loading to the stripline resonator;
monitoring a resonant characteristic of the stripline resonator; and
providing the loading signal in response to the resonant characteristic.

17. An apparatus for monitoring fluid in a fluid line, the apparatus comprising:

a dielectrically loaded transmission electromagnetic sensing device coupled to a segment of the fluid line such that the segment and fluid therein form part of the dielectric loading on the sensing device, the sensing device having a delay which varies in response to the dielectric loading and provides a sensor signal representative of the delay;

a flow data source which provides a flow signal representative of the volumetric flow rate of the fluid in the fluid line;

a processor, having predetermined gas data representative of a gas in the fluid, which receives the sensor signal from the sensing device and in response to the delay, provides a loading signal representative of the dielectric loading, compares the loading signal to the predetermined gas data to detect the presence of the gas and upon detecting the gas, determines the time period that the sensing device detects the gas, processes the detection time period with the flow signal and provides a signal indicative of the size of the gas bubble.

18. A method of monitoring fluid in a fluid line, comprising the steps of:

disposing a segment of the fluid line such that it and the fluid therein provide dielectric loading on a transmission electromagnetic sensing device, the delay through which varies in response to the dielectric loading;

sensing the delay of the sensing device;

providing a loading signal which is representative of the sensed delay of the sensing device;

sensing the volumetric flow rate of the fluid in the fluid line and providing a flow signal representative of the rate; and comparing the loading signal to predetermined gas data which is representative of a gas in the fluid, to detect the presence of the gas and upon detecting the gas, processing the time period that the gas is detected with the flow signal and providing a signal indicative of the size of the gas bubble passing through the fluid line in response to the comparison.

* * * * *